(12) United States Patent
Lawson et al.

(10) Patent No.: US 6,503,522 B2
(45) Date of Patent: *Jan. 7, 2003

(54) TERTIARY AMIDE-TERMINATED POLYAMIDES IN STRUCTURED PERSONAL CARE COMPOSITIONS

(75) Inventors: Nelson E. Lawson, Savannah, GA (US); Mark S. Pavlin, Savannah, GA (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/893,317

(22) Filed: Jun. 27, 2001

(65) Prior Publication Data

US 2002/0037993 A1 Mar. 28, 2002

Related U.S. Application Data

(63) Continuation-in-part of application No. 09/225,889, filed on Jan. 4, 1999, now Pat. No. 6,268,466.

(51) Int. Cl.$^7$ ........................... C08G 69/02; C08G 69/26
(52) U.S. Cl. ................ 424/401; 424/70.21; 424/70.17; 424/70.1; 424/64; 528/339; 528/339.3; 528/335; 528/332
(58) Field of Search ................. 528/335, 339, 528/332, 339.3; 424/401, 64, 70.1, 70.17, 70.21

(56) References Cited

U.S. PATENT DOCUMENTS

| | | |
|---|---|---|
| 2,379,413 A | 7/1945 | Bradley |
| 2,450,940 A | 10/1948 | Cowen et al. |
| 2,662,068 A | 12/1953 | Floyd |
| 2,861,048 A | 11/1958 | Wright et al. |
| 3,141,787 A | 7/1964 | Goetze et al. ............. 106/252 |
| 3,148,125 A | 9/1964 | Strianse et al. ............. 167/85 |
| 3,156,572 A | 11/1964 | Carlick et al. ............. 106/27 |
| 3,341,465 A | 9/1967 | Kaufman et al. ............. 252/316 |
| 3,420,789 A | 1/1969 | Wilson |
| 3,595,816 A | 7/1971 | Barrett |
| 3,615,289 A | 10/1971 | Felton ............. 44/7.5 |
| 3,645,705 A | 2/1972 | Miller et al. ............. 44/7.5 |
| 3,819,342 A | 6/1974 | Gunderman et al. ............. 44/7.5 |
| 4,051,159 A | 9/1977 | Tsoucalas et al. |
| 4,062,819 A | 12/1977 | Mains et al. |
| 4,128,436 A | 12/1978 | O'Hara et al. ............. 106/243 |
| 4,150,002 A | 4/1979 | Drawert et al. |
| 4,259,183 A | 3/1981 | Cadotte ............. 210/654 |
| 4,275,054 A | 6/1981 | Sebag et al. ............. 424/65 |
| 4,337,298 A | 6/1982 | Karim et al. ............. 428/461 |
| 4,341,671 A | 7/1982 | Bolze et al. ............. 528/324 |
| 4,376,194 A | 3/1983 | Tanaka et al. ............. 528/288 |
| 4,438,240 A | 3/1984 | Tannaka et al. ............. 525/420 |
| 4,552,693 A | 11/1985 | Hussain et al. ............. 252/522 A |
| 4,571,267 A | 2/1986 | Drawert et al. ............. 106/27 |
| 4,663,428 A | 5/1987 | Okitu et al. ............. 528/324 |
| 4,742,128 A | 5/1988 | Frisch et al. ............. 525/424 |

(List continued on next page.)

FOREIGN PATENT DOCUMENTS

| | | |
|---|---|---|
| EP | 467 533 A1 | 1/1992 |
| EP | 469 435 A1 | 2/1992 |
| EP | 1 068 855 A1 | 1/2001 |
| EP | 1 068 856 A1 | 1/2001 |
| WO | WO 98/17243 | 4/1998 |
| WO | WO 98/17705 | 4/1998 |

OTHER PUBLICATIONS

Téth et al., "Analytical Performances of Lipophilic Diamides Based Alkaline Earth Ion–Selective Electrodes," *Electroanalysis* 5(9–10):781–790, 1993.

Vedanayagam et al., "Kinetics of Reaction of $C_{36}$ Dimeric Fatty Acids and Ethylenediamine in Solution," *J. Applied Polymer Science* 45(12):2245–2248, 1992.

Yasuda et al., "Novel Low–molecular–weight Organic Gels: N, N', N"–Tristearyl trimesamide/Organic Solvent System," *Chemistry Letters*:575–576, 1996.

Primary Examiner—Fred Zitomer
(74) Attorney, Agent, or Firm—Seed Intellectual Property Law Group PLLC

(57) ABSTRACT

A structured, solid composition that contains at least one colorant, a liquid oil phase, and a gellant, wherein the gellant is a tertiary amide-terminated polyamide resin (ATPA) of the formula (1):

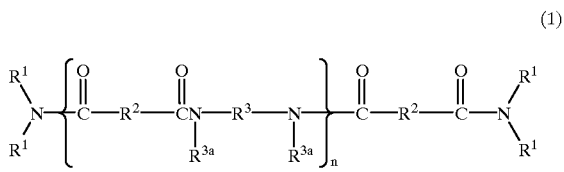

(1)

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid; the liquid oil phase and the ATPA resin forming a physiologically acceptable medium. The composition may be formulated into a cosmetic or other personal care product, for instance, a black mascara, eye liner, foundation, lipstick, blush, deodorant or make-up remover, body make-up, eye shadow or rouge, or concealer.

32 Claims, No Drawings

U.S. PATENT DOCUMENTS

| | | | |
|---|---|---|---|
| 4,742,147 A | 5/1988 | Nichols | 528/75 |
| 4,760,117 A | 7/1988 | Evans et al. | 525/394 |
| 4,769,285 A | 9/1988 | Tasmussen | 428/355 |
| 4,816,549 A | 3/1989 | Rumack | 528/336 |
| 4,937,069 A | 6/1990 | Shin | 424/66 |
| 4,946,922 A | 8/1990 | Reisch et al. | 528/76 |
| 5,069,897 A | 12/1991 | Orr | 424/66 |
| 5,102,656 A | 4/1992 | Kasat | 424/66 |
| 5,177,177 A | 1/1993 | Thullen et al. | 528/339.3 |
| 5,342,894 A | 8/1994 | Robeson et al. | 525/183 |
| 5,364,924 A | 11/1994 | Gerkin et al. | 528/73 |
| 5,372,852 A | 12/1994 | Titterington et al. | 427/288 |
| 5,432,204 A | 7/1995 | Farkas | 521/49 |
| 5,500,209 A | 3/1996 | Ross et al. | 424/66 |
| 5,538,718 A | 7/1996 | Aul et al. | 424/64 |
| 5,603,925 A | 2/1997 | Ross et al. | 424/65 |
| 5,645,632 A | 7/1997 | Pavlin | 106/31.29 |
| 5,783,657 A | 7/1998 | Pavlin et al. | 528/310 |
| 6,268,466 B1 | 7/2001 | MacQueen et al. | 528/335 |

TERTIARY AMIDE-TERMINATED POLYAMIDES IN STRUCTURED PERSONAL CARE COMPOSITIONS

CROSS-REFERENCE TO RELATED APPLICATION

This application is a continuation-in-part of U.S. patent application Ser. No. 09/225,889, filed Jan. 4, 1999, now U.S. Pat. No. 6,268,466 and allowed, which application is incorporated herein by reference in its entirety.

TECHNICAL FIELD

The present invention pertains to a skincare or skin treatment composition which can be used as make-up for the skin, the scalp, and/or for lips for human beings, containing a fatty liquid phase gelled by a particular gellant and presented in the form of a stick which, when applied, gives a gloss coating and which does not run or wick.

BACKGROUND OF THE INVENTION

In cosmetic or skincare products, it is usual to find a structured fatty liquid phase, i.e., a thickened, gelled, or solidified phase. This is the case in particular in solid compositions such as deodorants, balms and lipsticks, concealers for shadows under the eyes and molded foundations. Structure is typically obtained by introducing waxes or charged species into the formulation. Unfortunately these waxes and/or charged species have a tendency to make the coatings of the composition have a matte appearance which is not always desirable, especially for lipstick since women prefer a lipstick that gives more gloss to the lips.

The structure of the fatty liquid phase also limits its exudation (or running) from solid compositions and furthermore limits wicking of liquid into any wrinkles and fine lines after its application to the skin or the lips, a performance property which is particularly in demand for a lipstick. Too much wicking of the fatty liquid phase, especially if it is highly colored, gives an inaesthetic effect around the lips, particularly bringing out the wrinkles and fine lines. This is often specified by women as the main drawback of classical lipsticks.

Gloss is essentially dependent on the nature of the fatty liquid phase. It is possible to decrease the amount of waxes and charged species in the composition to obtain greater gloss in a lipstick, but then the running and wicking of the fatty liquid phase increases. In other words, the amount of waxes and charged species necessary for the realization of a sufficiently firm, run-free stick decreases the gloss of the coating.

The invention bears precisely on the composition of a face and/or lip care and/or makeup and/or treatment allowing to remedy these disadvantages.

SUMMARY OF THE INVENTION

In one aspect, the present invention provides a structured, i.e., gelled, solid composition that contains at least one colorant, a continuous liquid oil phase, and a gellant wherein the gellant for the continuous liquid oil phase is a tertiary amide-terminated polyamide (ATPA) resin of the formula (1):

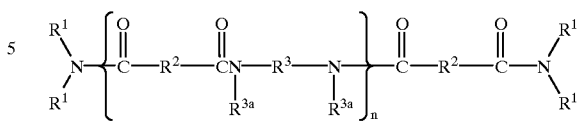

(1)

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid; the composition being essentially free of hydrocarbon wax; and the colorant, the liquid oil phase and the ATPA resin forming a physiologically acceptable medium.

In another aspect, the present invention provides a structured composition that contains at least one colorant, a continuous liquid oil phase and a gellant, wherein the continuous liquid oil phase gellant is a tertiary amide-terminated polyamide (ATPA) resin of the formula (1):

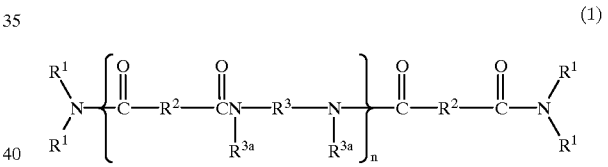

(1)

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the atom to which $R^3$ and $R^{3a}$ are both bonded is part of a heterocyclic structure defined in part by $R^{3a}$—N—$R^3$, the composition being in the form of a solid with a hardness of 20 to 2,000 g the composition being essentially free of hydrocarbon wax; the colorant, the liquid oil phase and the ATPA resin forming a physiologically acceptable medium.

In another aspect, the present invention provides a structured solid composition for making up the skin or lips, where the composition contains at least one pigment in sufficient quantity for making up the skin or lips, a liquid continuous oil phase, and a gellant wherein the gellant for the liquid continuous oil phase is a tertiary amide-terminated polyamide (ATPA) resin of the formula (1):

(1)

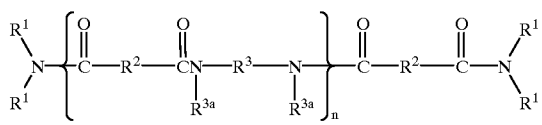

wherein, n designates a number of repeating units such that terminal amide groups constitute from 10% to 50% of the total amide groups; $R^1$ at each occurrence is independently selected from a $C_{4-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid; wherein the pigment, the liquid oil phase and the ATPA resin form a physiologically acceptable medium.

In another aspect, the present invention provides a structured composition for making up the skin or lips, where the composition includes at least one pigment in sufficient quantity for making up the skin or lips, a liquid continuous oil phase, and a gellant, wherein the gellant for the continuous oil phase is a tertiary amide-terminated polyamide (ATPA) resin of the formula (1):

(1)

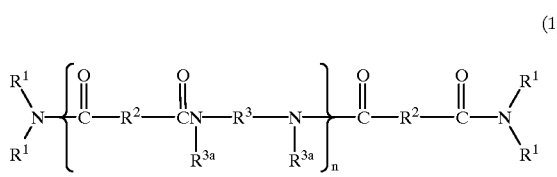

wherein, n designates a number of repeating units such that terminal amide groups constitute from 10% to 50% of the total amide groups; $R^1$ at each occurrence is independently selected from a $C_{4-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid with hardness of 20 to 2000 g; and wherein the pigment, the liquid oil phase and the ATPA resin form a physiologically acceptable medium.

In another aspect, the present invention provides a structured lipstick composition that contains at least one pigment in sufficient quantity for making up the skin or lips, a liquid continuous oil phase, and a gellant, wherein the gellant for the liquid continuous oil phase is a tertiary amide-terminated polyamide (ATPA) resin of the formula (1):

(1)

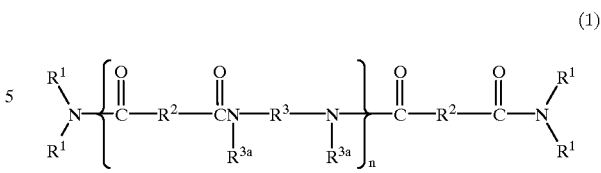

wherein, n designates a number of repeating units such that terminal amide groups constitute from 10% to 50% of the total amide groups; $R^1$ at each occurrence is independently selected from a $C_{4-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a self-support solid; and the pigment, the liquid oil phase and the ATPA resin form a physiologically acceptable medium.

In another aspect, the present invention provides a stick for making up the skin or lips. The stick contains, at a minimum, at least one pigment in sufficient quantity for making up the skin or lips, a liquid continuous oil phase, and a gellant wherein the gellant for the liquid continuous oil phase is a tertiary amide-terminated polyamide (ATPA) resin of the formula (1):

(1)

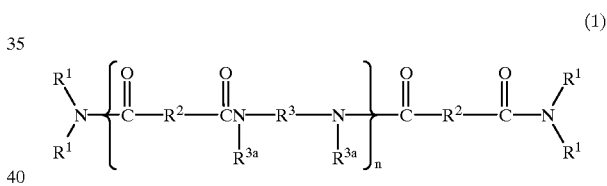

wherein, n designates a number of repeating units such that terminal amide groups constitute from 10% to 50% of the total amide groups; $R^1$ at each occurrence is independently selected from a $C_{4-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, and wherein the pigment, the oil phase and the ATPA resin form a physiologically acceptable medium.

In various further aspects, one or more the following criteria apply in describing the above-identified invention, where each criterion is applied independently, unless such application would be inconsistent: The composition is self-supporting. $R^1$ at each occurrence is independently selected from a $C_{4-22}$ hydrocarbon group. $R^2$ at each occurrence is independently selected from a $C_{4-42}$ hydrocarbon group. $R^2$ at each occurrence is independently selected from a $C_{2-42}$ hydrocarbon group, where at least 50% of the $R_2$ groups have 30–42 carbon atoms. The composition also contains at least one liquid amphiphilic compound having, at ambient temperature, an HLB value of less than 12. The composition is in the form of a solid with a hardness of 20 to 2,000 g. The composition has a hardness of from 20 g to 900 g. The composition is essentially free of hydrocarbon wax, where "essentially free" means that the presence of the hydrocarbon wax does not materially effect the properties of the composition. The colorant, the liquid oil phase and the ATPA resin form a physiologically acceptable medium. The composition also contains at least one liquid amphiphilic compound having, at ambient temperature, an HLB value of from 1 to 7. The composition also contains at least one liquid amphiphilic compound having, at ambient temperature, an HLB value of from 1 to 5. The amphiphilic compound has both a polar part and a lipophilic part, wherein the lipophilic part includes a carbon chain containing at least 8 carbon atoms, preferably from 18 to 28 carbon atoms. The polar part is the reaction product of a compound selected from alcohols and polyols containing 1 to 12 hydroxyl groups, polyoxyalkylenes up to 20 propoxylation moieties and up to 20 oxyethylene moieties. The amphiphilic compound is selected from esters of hydroxystearate, oleate or isostearate with one or more of glycerol, sorbitan, methylglucose, and octyldodecanol. The amphiphilic compound represents 0.1 to 36% of the total weight of the composition. The amphiphilic compound represents 2 to 15% of the total weight of the composition. The ATPA resin represents 0.5 to 80% of the total weight of the composition. The ATPA resin represents 5 to 40% of the total weight of the composition. The liquid oil phase contains more than 40% of one or more apolar liquid oils. The liquid oil phase contains at least one hydrocarbon oil of mineral or synthetic origin. The oil phase contains at least one apolar oil chosen from parleam oil, isoparaffins, squalane and their mixtures. The liquid oil phase represents 20 to 75% of the total weight of the composition. The composition is formulated as a composition for the care and/or treatment and/or makeup of keratinous matter. The composition also contains at least one cosmetic or dermatological active ingredient. The composition also contains at least one additive selected from water, antioxidants, essential oils, preservatives, neutralisers, liposoluble polymers, additives, flavors and their mixtures. The composition is in the form of a transparent anhydrous rigid gel. The colorant represents 5 to 25% of the total weight of the composition. The composition is self-supporting. The composition is formulated into a cosmetic or other personal care product, for instance, a black mascara, eye liner, foundation, lipstick, blush, deodorant or make-up remover, body make-up, eye shadow or rouge, or concealer.

The forgoing summary presents some noteworthy aspects of the present invention, where these and additional aspects and features of the present invention are described in more detail below.

DETAILED DESCRIPTION OF THE INVENTION

Surprisingly the applicant has found that the use of a certain gellant, specifically a resin referred to herein as ATPA, builds structure in the fatty liquid phases present in personal care and other cosmetic formulations, even in the absence of wax. Thus, even when the composition is in the form of a firm stick, the composition, when applied to the skin or lips, results in a glossy coating without running or wicking. More particularly, in one aspect, the present invention provides a structured composition containing at least one coloring component and a continuous fatty, also referred to herein as oily, liquid phase gelled by at least one gellant, including an ATPA resin, the composition being an essentially waxless solid, where the coloring component, fatty liquid phase and the ATPA gellant forms an acceptable physiological medium.

By fatty liquid phase, in the meaning of the present application, is meant a liquid at ambient temperature (25° C.) and an atmospheric pressure (760 mm of Hg), composed of either one or several compatible fats or fat-derived materials, or materials having properties similar to fats, commonly known also as oils.

A wax, in the meaning of the present invention, is a opaque or translucent lipophilic material, solid at ambient temperature (25° C.), having a sharp, that is, well-defined reversible solid to liquid transition between 40° C. and 200° C., and having in the solid state an anisotrope crystalline organization. The crystal facets are such that the crystals diffract and/or diffuse light making the composition look cloudy, more or less opaque. When the wax is brought to its melting temperature, it is possible to mix it with the continuous fatty phase and to effect a homogeneous mixture, but when the temperature is returned to ambient, re-crystallization of the wax in the oils of the mixture occurs. It is this re-crystallisation which is responsible for both the mixture's structure and also for its reduction in gloss. In one aspect, the present invention provides composition that are essentially free of wax, by which it is meant that the composition does not contain sufficient quantity of wax that the wax is able to noticeably impact the structuring of the composition. In another aspect, the composition contains no wax.

The waxes in the meaning of the application are those generally used in the cosmetic and skin treatment field; they are in particular those of natural origin such as beeswax, Carnauba wax, Candelilia wax, Ouricoury wax, Japan wax, cork or sugar cane fibres, paraffin, lignite waxes, lanolin wax, Montan wax, ozocerites, hydrogenated oils such as hydrogenated jujuba oil, but also synthetically produced waxes such as polyethylene wax, resulting from the polymerisation of ethylene, the synthetically obtained waxes of Fischer-Tropsch, microcrystalline waxes, the esters of fatty acids and glycerides, and the silicone waxes such as alkyl, alkoxy and/or esters of poly(di)methyl siloxane, which are solid at 40° C.

The composition of the invention is preferably presented as a stick, which may be free-standing, or in a container, e.g. a jar or pot. In one aspect the composition is an anhydrous transparent rigid gel and more especially in the form of a transparent anhydrous stick. The structure imparted to the fatty liquid (or oil) phase by the ATPA resin is such that for formulations having a sufficient concentration of the ATPA, a rigid structure is obtained which can be formed into a stick. These sticks, once colored, produce, once applied, a glossy coating of a homogeneous color and with no wicking into the wrinkles and fine lines of the skin which surround the lips in particular, but also the eyes. The ATPA gellants which are useful in the present invention are soluble in a great many different oils.

The invention also concerns a structured composition for make-up, lips or hair and nails containing at least one pigment in sufficient quantity to make up the skin, lips and/or hair and nails and a fatty liquid phase structured by at least one gellant including ATPA resin, which composition is in the form of a self-supporting solid and has a hardness in a range from 20 to 2000 g and preferably 20 to 900 g and more preferably 20 to 600 g, where the pigment, the liquid fatty phase and the ATPA gellant form an acceptable physiological medium.

By "pigment" is understood any insoluble solid particle in the medium used for giving and/or modifying a color and/or an iridescent aspect.

The gellant useful in the present invention includes at least a resin comprising short-chain polyamides of the formula (1), which will be referred to herein as tertiary amide-terminated polyamides, or ATPAs.

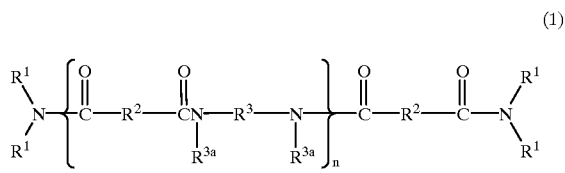

(1)

In formula (1), n designates a number of repeating units such that terminal (i.e., $R^1$-containing) amide groups constitute from 10% to 50% of the total of the amide groups shown in formula (1); $R^1$ at each occurrence is independently selected from a $C_{1-22}$ hydrocarbon group; $R^2$ at each occurrence is independently selected from a $C_{2-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

Preferably, the resin composition further comprises diamide having formula (1) wherein n=0, such that the ratio of terminal amide groups to the sum of amide groups in the total of the molecules that comprise the resin of formula (1) is from 0.1 to 0.7. Preferably, the resin composition is at reaction equilibrium.

As may be seen from formula (1), the ATPA resins have terminal amide groups of the formula —C(=O)N($R^1$)($R^1$) at both ends of a series of amide groups. These terminal amide groups are formed from secondary amines (since $R^1$ is an organic group and is not hydrogen), and therefore the terminal amide groups in formula (1) are properly referred to as tertiary amide groups. Accordingly, the ATPA resins may be referred to as tertiary amide-terminated polyamides.

The letter "n" in formula (1) designates the number of repeating units present in a molecule of ATPA, and is an integer greater than 0. According to the invention, n may be 1, in which case the ATPA contains equal numbers of terminal amide and non-terminal amide groups, i.e., the terminal amide groups constitute 50% of the total of the amide groups in the ATPA molecule. The preferred ATPA resins are of relatively low molecular weight, so that n is preferably 1 to about 10, and more preferably is 1 to about 5. Because the ATPA molecules have such a low molecular weight, they could equally well be referred to as tertiary amide-terminated oligoamides. In any event, viewed another way, the terminal amide groups constitute about 10% to about 50%, preferably about 15% to about 40%, and more preferably about 20% to about 35% of the total of the amide groups. A preferred ATPA resin includes a mixture of ATPA molecules of formula (1) having various n values. The ATPA resin has a weight average molecular weight of less than about 10,000, and typically less than about 5,000, but more than 500, typically more than 1,000, when measured by gel permeation chromatography using polystyrene calibration standards.

The $R^1$ group in formula (1) is a hydrocarbon group, and preferably is an alkyl or alkenyl group that contains at least 1, typically at least 4, and preferably more than 4 carbon atoms, e.g., 8, 10, 12, 14, 16, 18, 20, or 22 carbon atoms. Alkyl groups are preferred, however alkenyl groups having 1–3, and preferably 1 site of unsaturation are also suitable. The upper range for the number of carbon atoms in the $R^1$ group is not particularly critical, however preferably the $R^1$ group has less than or equal to about 22 carbon atoms. $R^1$ groups having about 16–22 carbon atoms are highly preferred. The identity of $R^1$ at any occurrence is independent of the identity of $R^1$ at any other occurrence.

Suitable $R^1$ groups are readily introduced into a molecule of formula (1) when secondary monoamine(s) is used as a co-reactant in preparing the ATPA resin. The secondary monoamine has the formula $HN(R^1)(R^1)$, wherein $R^1$ is defined above. Suitable secondary monoamines are commercially available from a variety of sources, including Witco Corporation (Greenwich, Conn.; http://www.witco.com); Akzo Nobel Chemicals, Surface Chemistry (Chicago, Ill.; http://www.akzonobelusa.com); and Aldrich (Milwaukee, Wis.; http://www.aldrich.sial.com). Di(hydrogenated tallow) amine is a preferred secondary monoamine.

The $R^2$ group in formula (1) is suitably a hydrocarbon containing 2 to 42 carbon atoms, and preferably contains 4 to 42 carbon atoms. A more preferred $R^2$ group contains 30–42 carbon atoms (i.e., is a $C_{30-42}$ group), and at least 50% of the $R^2$ groups in an ATPA resin preferably have 30–42 carbon atoms. Such $R^2$ groups are readily introduced into an ATPA when the resin is prepared from polymerized fatty acid, also known as dimer acid. Polymerized fatty acid is typically a mixture of structures, where individual dimer acids may be saturated, unsaturated, cyclic, acyclic, etc. Thus, a detailed characterization of the structure of the $R^2$ groups is not readily available. However, good discussions of fatty acid polymerization may be found in, for example, U.S. Pat. No. 3,157,681 and Naval Stores-Production, Chemistry and Utilization, D. F. Zinkel and J. Russel (eds.), Pulp. Chem. Assoc. Inc., 1989, Chapter 23. Dimer acid is available commercially as, for example, UNIDYME™ dimer acid Arizona Chemical Company, a company of International Paper, (Panama City, Fla.), EMPOL™ dimer acid from Henkel Corporation, Emery Oleochemicals Division (Cincinnati, Ohio); PRIPOL™ dimer acid from Unichema North America (Chicago, Ill.), and SYLVADYM™ dimer acid from Arizona Chemical Company, a company of International Paper, (Panama City, Fla.).

While the preferred ATPA resins contain at least 50% $C_{30-42}$ groups as the $R^2$ group, more preferably the total of the $R^2$ groups consist of at least 75% $C_{30-42}$ groups, and still more preferably consist of at least 90% $C_{30-42}$ groups. ATPA resins of formula (1) wherein $R^2$ is entirely $C_{30-42}$ are preferred gelling agents of the invention.

However, ATPA resins may also contain $R^2$ groups having less than 30 carbon atoms. For example, an ATPA resin may contain one or more $R^2$ groups having about 4 to 19, preferably about 4 to 12, and more preferably about 4 to 8 carbon atoms. The carbon atoms may be arranged in a linear, branched or cyclic fashion, and unsaturation may be present between any two carbons. Thus, $R^2$ may be aliphatic or aromatic. When present, these lower carbon-number $R^2$ groups are preferably formed entirely of carbon and hydrogen, i.e., are hydrocarbyl groups. Such lower carbon-number $R^2$ groups preferably constitute less than 50% of the $R^2$ groups; however, when present, constitute about 1% to about 50%, and preferably about 5% to about 35% of the total of the $R^2$ groups. The identity of $R^2$ at each occurrence is independent of the identity of $R^2$ at any other occurrence. Suitable co-diacids are available from, for example, Aldrich (Milwaukee, Wis.).

The —N($R^{3a}$)—$R^3$—N($R^{3a}$)— group in formula (1) links two carbonyl (C=O) groups. In a preferred embodiment of the invention, all of the $R^{3a}$ groups in an ATPA resin are hydrogen, so that $R^3$ alone joins the two nitrogen atoms shown in the formula —N($R^{3a}$)—$R^3$—N($R^{3a}$)—. In this case, the $R^3$ group contains at least two carbon atoms, and optionally oxygen and/or nitrogen atoms, in addition to any hydrogen atoms that are necessary to complete otherwise unfilled valencies of the carbon, oxygen and nitrogen atoms. In one embodiment, $R^3$ is a hydrocarbon group, having 2 to about 36 carbon atoms, preferably having 2 to about 12 carbon atoms, and more preferably having 2 to about 8 carbon atoms. These carbon atoms may be arranged in a linear, branched or cyclic fashion, and unsaturation may be present between any two of the carbon atoms. Thus, $R^3$ may contain aliphatic or aromatic structures. The identities of $R^3$ and $R^{3a}$ at each occurrence are independent of their identities at any other occurrence.

The $R^3$ groups may contain oxygen and/or nitrogen in addition to carbon and hydrogen atoms. A typical oxygen atom-containing $R^3$ group is a polyalkylene oxide, i.e., a group having alternating alkylene groups and oxygen atoms. Indeed, the oxygenation in a $R^3$ group is preferably present as an ether group. Representative polyalkylene oxides include, without limitation, polyethylene oxide, polypropylene oxide and copolymers (either random, alternating or block) of ethylene oxide and propylene oxide. Such oxygenated $R^3$ groups are readily introduced into an ATPA resin through use of JEFFAMINE™ diamines (Huntsman Chemical, Inc., Houston, Tex.). These materials are available in a wide range of molecular weights, where any molecular weight diamine may be used in the preparation of the resins of the invention. While some of the $R^3$ groups may contain oxygen (at least about 1%), preferably a minor number (less than 50%) of the $R^3$ groups contain oxygen, and more preferably less than about 20% of the $R^3$ groups contain oxygen. The presence of oxygen-containing $R^3$ groups tends to lower the softening point of the ATPA resin.

When present, the nitrogen atoms in an $R^3$ group are preferably present as secondary or tertiary amines. A typical nitrogen-containing $R^3$ group having secondary amine groups is a polyalkylene amine, i.e., a group containing alternating alkylene groups and amine groups, which is sometimes referred to as a polyalkylene polyamine. The alkylene group is preferably a lower alkylene group, e.g., methylene, ethylene, (i.e., —CH$_2$CH$_2$—), propylene, etc. A typical polyalkylene amine may be represented by the formula —NH—(CH$_2$CH$_2$NH)$_m$CH$_2$CH$_2$—NH— wherein m is an integer from 1 to about 5.

However, the nitrogen atoms in the nitrogen-containing $R^3$ group may alternatively (or additionally) be present as tertiary nitrogen atoms, e.g., they may be present in a heterocycle of the formula:

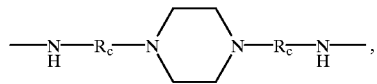

wherein $R_c$ is a $C_{1-3}$ alkylene group.

In the above-described nitrogen-containing $R^3$ groups, $R^{3a}$ was hydrogen. However, $R^{3a}$ is not limited to hydrogen. In fact, $R^{3a}$ may be a $C_{1-10}$alkyl group, preferably a $C_{1-5}$alkyl group, and more preferably a $C_{1-3}$alkyl group. In addition, $R^3$ and $R^{3a}$, or two $R^{3a}$ groups, may together form a heterocyclic structure, e.g., a piperazine structure such as

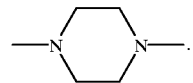

In this case, the two $R^{3a}$ groups may be seen as joining together to form an ethylene bridge between the two nitrogen atoms, while $R^3$ is also an ethylene bridge. Additional suitable diamines are available from, for example, Aldrich (Milwaukee, Wis.).

The ATPA resin typically includes a mixture of ATPA molecules of formula (1) in addition to, for example, by-products that are formed during the ATPA-forming reaction. While the ATPA molecules of formula (1) may be purified from such by-products using, for example, chromatography or distillation, the by-products are typically either minimal in amount or impart desirable properties to the resin when the resin functions as a gelling agent, and thus need not be separated from the molecules of formula (1) in order for a suitable ATPA resin to be formed.

As described herein, amines and carboxylic acids are preferred starting materials to form the ATPA resins of the invention. These starting materials are preferably reacted together with a stoichiometry, and under reaction conditions, such that the acid number of the resulting ATPA resin is less than 25, preferably less than 15, and more preferably less than 10, while the amine number is preferably less than 10, more preferably less than 5, and still more preferably less than 1. The softening point of the ATPA resin is preferably greater than room temperature, more preferably is about 50° C. to about 150° C., and still more preferably is about 80° C. to about 130° C.

It is important to control the stoichiometry of the reactants in order to prepare an ATPA resin according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dicarboxylic acid (e.g., sebacic acid) has two equivalents of carboxylic acid, while a mole of monoamine has one equivalent of amine. Furthermore, it is emphasized that in preparing an ATPA resin, the diacid has only two reactive groups (both carboxylic acids), the monoamine has only one reactive group (a secondary amine group) and the diamine has only two reactive groups (preferably both primary amines), and these are preferably, although not necessarily, the only reactive materials present in the reaction mixture.

When co-diacid is employed to prepare an ATPA resin, the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0–30 equivalent percent, and more preferably contributes 0–10 equivalent percent of the acid equivalents in the reaction mixture.

The stoichiometry of the reactants will have a significant impact on the composition of the ATPA resin. For example, ATPA resins made with increasing amounts of secondary monoamine will tend to have lower (number and weight) average molecular weights. In other words, as more monofunctional reactant is used, the number of amide pairs in an average molecule of formula (1) will decrease. On the other hand, as less monoamine is used, the average molecular weight of the molecules in the ATPA resin will increase. In general, increasing the average molecular weight of the ATPA will tend to increase the melting point and melt viscosity of the resin. When a high melting point ATPA is combined with an oil phase to thereby form a gel, the gel will tend to have a firmer consistency than does a gel formed from an ATPA with a low melting point.

In order to prepare an ATPA resin, the above-described reactants (diacid, monoamine and diamine, or reactive equivalents thereof) may be combined in any order. Preferably, the reactants are simply mixed together and heated for a time and at a temperature sufficient to achieve essentially complete reaction, to thereby form the ATPA resin. During formation of the ATPA resin, the diacid and diamine groups will alternate to form what may be termed an alternating copolymer. The ATPA is not a block copolymer. The terms "complete reaction" and "reaction equilibrium" as used herein have essentially the same meaning, which is that further heating of the product gelling agent does not result in any appreciable change in the acid or amine numbers of the resin.

Thus, the ATPA resin may be formed in a one-step procedure, wherein all of the diacid (including co-diacid), secondary monoamine, and diamine are combined and then heated to about 180–250° C. for a few hours, typically 2–8 hours. When lower temperatures are used, a longer reaction time is typically needed to achieve complete reaction. When the reaction temperature is too high, the reactants and/or products may undergo undesirable thermally-induced decomposition. Since one or more of the reactants may be a solid at room temperature, it may be convenient to combine each of the ingredients at a slightly elevated temperature, and then form a homogeneous mixture prior to heating the reaction mixture to a temperature sufficient to cause reaction between the diacid, monoamine and diamine. Alternatively, although less preferably, two of the reactants may be combined and reacted together, and then the third reactant is added followed by further heating until the desired product is obtained. Reaction progress may be conveniently monitored by periodically measuring the acid and/or amine number of the product mixture.

As one example, dimer acid may be reacted with diamine so as to form polyamide, and then this intermediate polyamide may be reacted with monoamine to form a tertiary amide-terminated dimer acid-based polyamide. Or, dimer acid may be reacted with the monoamine to thereby form diamide, and this diamide may be reacted with diamine to thereby form tertiary amide-terminated dimer acid-based polyamide. Because the components of the ATPA resin are preferably in reaction equilibrium (due to transamidation), the order in which the reactants are combined typically does not impact on the properties of the gelling agent.

Any catalyst that may accelerate amide formation between carboxylic acid and amine groups may be present in the reaction mixture described above. Thus, mineral acid such as phosphoric acid, or tin salts such as dibutyltin oxide, may be present during the reaction. In addition, it is preferred to remove water from the reaction mixture as it is formed upon amide formation. This is preferably accomplished by maintaining a vacuum on the reacting mixture, or by passing a gentle stream of an inert gas (e.g., nitrogen) across the top of the reaction mixture.

Advantageously, the ATPA gellant is associated with at least one amphiphilic liquid component at ambient temperature, with a hydrophilic/lipophilic balance (HLB) lower than 12 and especially from 1 to 7 and preferably from 1 to 5, and better 3 to 5. According to the invention, one or several amphiphilic components may be used, where these amphiphilic components are intended to reinforce the structuring properties of the polymer with heteroatoms, to facilitate the incorporation of the gellant into the composition and improve the coating capacity of the stick.

The amphiphilic compounds which can be used in the composition of the invention include a lipophilic part linked to a polar part, the lipophilic part comprising a carbon chain, having at least 8 carbon atoms, particularly from 18 to 32 carbon atoms and preferably from 18 to 28 carbon atoms. Preferably, the polar part of this or these amphiphilic components is the reaction residue of a component chosen from among the alcohols and polyols having from 1 to 12 hydroxyl group, the polyoxalkylenes having at least 2 oxyalkenated moieties and having from 0 to 20 oxypropylenated moieties and/or 0 to 20 oxyethylenated moieties. In one aspect, the amphiphilic component is an ester chosen among the reaction products of hydroxystearates, the oleates, or the isostearates with glycerol, sorbitan or methylglucose or the fatty alcohols in the C-12 to C-26 range such as octyldodecanol and mixtures of these. Among these esters, the monoesters and the mono- and di-ester mixtures are preferred.

The amount of amphiphilic component and that of the gellant are chosen according to the desired hardness of the gel and according to the particular application intended. According to the invention, the composition should have a hardness from 20 to 2000 g and better from 20 to 900 g, in particular from 20 to 600 g and for example from 150 to 450 g. This hardness may be measured by a method involving penetration with a probe into the composition and in particular with the help of a texture analyser (for instance TA-XT2 from Rheo) provided with an ebonite cylinder 25 mm high and 8 mm in diameter. The hardness measurement is done at 20° C. at the centre of 5 samples of the composition. The cylinder is introduced into each sample of the composition at a first speed of 2 mm/s, then at a speed of 0.5 mm/s and finally at 2 mm/s, the total displacement being 1 mm. The hardness value recorded is that of the maximum peak. The error margin is +/−50 g.

The hardness may also be measured by the so-called cheesewire method that consists of cutting an 8.1 mm stick of lipstick and measuring its hardness at 20° C. by means of a dynamometer DFGHS 2 of the company Indelco-Chatillon moving at a speed of 100 mm/min. It is expressed in terms of the cutting force (expressed in grams) needed to cut a stick in these conditions. According to this method, the hardness of a preferred composition of the present invention in a stick form varies from 30 to 150 g, preferably from 30 to 120 g and as an example from 30 to 50 g.

The hardness of a composition according to the invention is such that the composition is preferably self-supporting and can be easily pushed out to form a satisfying coating on the skin and the lips. Moreover, with this sort of hardness, the composition has good resistance to shocks. According to the invention, the composition in the form of a stick behaves like an elastic deformable and flexible solid, giving a remarkable elastic softness when applied. This property is particularly desirable when a composition of the present invention is formulated as a lipstick, and in a preferred aspect of the invention, the composition is formulated as a lipstick.

The respective quantities of gellant and of amphiphilic component are preferably such that a stick is obtained. In practice, the quantity of ATPA gellant represents from 0.5 to 80% of the total weight of the composition and preferably from 5 to 40%. The quantity of amphiphilic component represents practically from 0.1 to 35% of the total weight of the composition and preferably 2% to 15%.

Advantageously, the fatty liquid phase of the composition, excluding the ATPA resin, contains more than 50% and preferably more than 60% of liquid oils. In particular, the fatty liquid phase to be gelled by the ATPA resin contains a prevailing quantity, that is, greater than 50% of the total weight of the fatty liquid phase, of oil or mixture of non-polar oils.

In particular, the oils of the invention may be selected from:

hydrogenated vegetable oils with a high content in triglycerides consisting of fatty acid esters of glycerol in which the fatty acids may have various chain lengths, which can be linear, saturated or unsaturated; these oils include, wheatgerm, corn, sunflower, shea butter, castor oil, sweet almond, macadamia, apricot, soya, rapeseed, cotton, luzerne, poppy, Hokkaido squash, sesame, squash, avocado, hazelnut, grapeseed, or blackcurrant seed, evening primrose, millet, barley, quinoa, olive, rye, safflower, candlenut tree, passion flower, and Muscat rose, or triglycerides of caprilyc/capric acids such as those sold by the company Stearineries Dubois or those sold under the trade-names MIGLYOL™ 810,812 and 818 by the company Dynamit Nobel;

synthetic ester oils of the formula $R^5C(O)OR^6$ in which $R^5$ represents the remains of a fatty acid having from 1 to 40 and preferably 7 to 19 carbon atoms and $R^6$ represents a hydrocarbon chain containing 1 to 40 and preferably 3 to 20 carbon atoms, for example, oil of Purcellin (cetostearyl octanoate), isononyl isononanoate, alkyl benzoates in which the alkyl group has 10 to 18 carbon atoms, isopropyl myristate, ethyl 2-hexyl palmitate, octanoates, decanoates or ricinoleates of alcohols or polyalcohols; hydroxylated esters such as isostearyl lactate, di-(isostearyl) malate and the esters of pentaerythritol; long-chain alkyl ethers having from 10 to 40 carbon atoms; fatty alcohols having from 8 to 22 carbon atoms such as oleyl alcohol; and their mixtures.

Non-polar oils according to the invention are in particular hydrocarbons and fluorocarbon oils, linear, branched or cyclic, of synthetic or mineral origin, volatile or non-volatile, including for example paraffin oils such as isoparaffins and isododecane, vaseline, polydecenes, hydrogenated polyisobutene such as PARLEAM, squalene, squalane and mixtures of them. Preferred oils are of the hydrogenated type of mineral or synthetic origin, chosen in particular among the hydrocarbons, in particular the alcanes such as oil of Parleam, the isoparaffins among which are isododecane, squalane and their mixtures. The fatty liquid phase represents, practically, 5 to 99% of the total weight of the composition, preferably from 20 to 75%.

In one aspect, the composition which is the object of the invention can furthermore include other ingredients or additives commonly used in the domain in question, chosen in particular from water, possibly thickened or gelified by a thickener or an aqueous phase gelling agent antioxidants, the silicon-containing oils such as polydimethylsiloxanes (PDMS), linear or cyclic, liquid at ambient temperature, the plymethylsiloxanes having groupings of alkyls, alkoxy or phenyls pendent and/or at the end of the siliconated chain, groupings having each from 2 to 24 carbon atoms; the phenylated silicones like the phenyl trimethicones, the phenyl dimethicones, the phenyl trimethylisiloxysilicates; essential oils, preservatives, perfumes, insect repellents, neutralisers, liposoluble polymers, active cosmetic or skincare agents such as for instance, emollients, hydratants, vitamins, essential fatty acids, sun filters and mixtures of these. These additives may be present in the fatty liquid phase or not and may be present in the composition in a quantity from 0 to 20% of the total weight of the composition and preferably from 0 to 10%. Advantageously, the composition contains at least an active cosmetic or skincare agent.

The composition according to the invention may be presented in the form of a tinted composition for skin treatment or for the care of keratinic substances such as skin, lips and/or the hair and nails in the form of a sun protecting or body hygiene composition, in particular in the form of a deodorant or make-up remover in the form of a stick. It may be used in particular as a basic composition for treatment of the skin, the hair and nails of the lips (lip balms protecting the lips from the effects of cold weather and/or the sun and/or the wind, cream for improving the skin, nails or hair).

The composition described in the invention can also be presented as a colored product for make-up of the skin, in particular a foundation, having possibly also care or treatment properties, a blusher, rouge and eye-shadow, a concealer, an eye-liner, a product for body make-up; for lip make-up such as lipstick, possibly with care or treatment properties; for make-up of the nails and eyelashes in the form of a loaf mascara, the eyebrows and hair in the form of a pencil. In particular, the composition described in the invention may be a cosmetic product containing active cosmetic or skincare agents.

Of course the composition of the invention must be cosmetically or dermatologically acceptable, i.e., it must contain a physiologically non-toxic and acceptable medium that can be applied to the skin, the hair and nails and the lips of a human being. By cosmetically acceptable is meant, in the meaning of the invention, a composition attractive as to appearance, scent and touch.

According to the invention, the composition contains a coloring substance that may be chosen among lipophilic colorants, pigments and nacreous smaterials commonly used in cosmetic or skincare compositions. This coloring substance is generally present in a quantity of 0.01 to 40% of the total weight of the composition, preferably from 1 to 35% and even better from 5 to 25%.

Preferably, the coloring substance should contain pigments and/or nacreous colorants suitable to obtain a make-up which is not transparent, but modifies the appearance of the underlying skin, lips, hair or nails. Such a coloring substance, unlike soluble colorants, is also useful for reducing the sticking touch of the composition.

Liposoluble coloring agents are for instance Sudanese red, DCRed 17, DC Green G, beta-carotene, soya oil, Sudanese brown, DC Yellow 11, DC Violet 2, DC Orange 5, quinoleine yellow. They may represent from 0 to 20% of the weight of the composition and preferably from 0.1 to 6% (if they are used).

Pigments may be white or colored, mineral and/or organic, coated or uncoated. Among the mineral pigments may be titanium dioxide, surface-treated or untreated, oxides of zirconium or cerium, iron oxides, chrome oxides, manganese violet, ultramarine blue, chromium hydrate and ferrous blue. Among the organic pigments may be carbon black, D&C type pigments, and lacquers based on cochineal, barium, strontium, calcium aluminium carmine. The pigments may represent from 0 to 40%, preferably from 1 to 35% and best from 2 to 25% of the total weight of the composition.

Nacreous pigments (or nacres) may be chosen from white nacreous pigments such as mica coated with titanium oxide or bismuth oxychloride, or the colored nacreous pigments such as titanium oxide-treated mica with iron oxides, titanium oxide-treated mica with, in particular, ferrous blue or chromium oxide, titanium oxide-treated mica with an organic pigment of the type already named as well as nacreous pigments based on bismuth oxychloride. They may represent from 0 to 20% of the total weight of the composition and preferably from 0.1 to 15% (if used).

The composition in accordance with the invention can be manufactured by known processes, generally used in the cosmetics or dermatology fields. An inventive composition can be manufactured by the process that consists in heating the ATPA resin to at least its softening temperature, adding the amphiphilic compound(s), the colorants and additives, then mixing the complete mixture until a homogeneous mixture is obtained. The homogeneous mixture obtained can then be cast in an appropriate mould such as a lipstick mould or directly into the packaging article such as a jar, pot, case or compact.

A further aim of the invention is a cosmetic process for care, make-up or treatment of keratinous matter and particularly the skin, lips and skin appendages, including application on keratinous matter of the composition, particularly a cosmetic application as defined above.

A farther aim of the invention is the use of a sufficient quantity of at least one gellant including ATPA resin in a cosmetic composition or for the manufacture of a physiologically acceptable composition, free of wax and containing a fatty liquid (or oil) phase and a colorant, having sufficient structure so that the composition takes the form of a self-supporting solid and, in particular, a solid with hardness of 20 to 2,000 g and particularly 20 to 900 g, and preferably 20 to 600 g.

A further aim of the invention is the use of a fatty liquid (or oil) phase, structured mainly by a sufficient quantity of at least one gellant including ATPA resin, in a cosmetic composition or for the manufacture of a physiologically acceptable rigid composition, particularly self-supporting, and with, for example, hardness of 20 to 2,000 g and particularly 20 to 900 g, and preferably, for example, 20 to 600 g, free of wax, glossy and/or non-running.

A further aim of the invention is the use of a liquid fatty (or oil) phase, structured mainly by a sufficient quantity of at least one gellant including ATPA resin, in a cosmetic composition or for the manufacture of a physiologically acceptable composition containing a fatty liquid phase and a colorant, to structure the composition in the form of a self-supporting solid and with hardness of, for example, 20 to 2,000 g and particularly 20 to 900 g and, for example, 20 to 600.

A further aim of the invention is the use of a liquid fatty (or oil) phase, structured mainly by a sufficient quantity of at least one gellant including ATPA resin, in a cosmetic composition or for the manufacture of a physiologically acceptable composition as an agent for limiting migration or wicking of the said composition.

A further aim of the invention is a make-up stick for use on the skin, lips and/or skin appendages, and particularly the lips, containing at least one pigment in sufficient quantity for making up the skin, lips and/or skin appendages, and a liquid fatty (or oil) phase, structured by at least one gellant including ATPA resin, and with the pigment, the oil phase and the ATPA resin forming a physiologically acceptable medium.

The invention is applicable not only to make-up products such as lipstick, and lip pencils, but also to products for skin care and treatment, including the scalp and lips, such as sun-protection and insect-repellent products in the shape of a stick for the skin of the face or the lips, to make-up products for the skin of the face as well as body of human beings, such as foundation shaped into a stick or molded into pots, concealers for shadows under the eyes and products of ephemeral tattooing, products of corporal hygiene such as stick deodorants and products for eye make-up such as eyeliners in the form of pencils and loaf mascaras.

The invention is illustrated in more detail in the following examples. Percentages are given in weight.

EXAMPLES

In the following Examples, softening point was measured using a Model FP83HT Dropping Point Cell from Mettler Instruments, Mettler-Toledo International, Inc. (CH-8606 Greifensee, Switzerland; http://www.mt.com), with a heating rate of 1.5° C./min. Techniques to measure acid and amine numbers are well known in the art and need not be described here. See, e.g., ASTM D-465 (1982) from American Society for Testing and Materials (West Conshohocken, Pa.; http://www.astm.org).

EXAMPLE 1

Tertiary Amide-Terminated Polyamides (ATPA)

Several ATPA's (labeled ATPA A, B, and C) were made from the reactants, and relative amounts thereof, as set forth in Table 1. In Table 1, "DTA" is an abbreviation for di(hydrogenated tallow) amine, "EDA" is an abbreviation for ethylene diamine, "SA" is an abbreviation for stearyl amine, and PD-23™ is a petroleum distillate, all available from Witco Corporation (Greenwich, Conn.; http://www.witco.com). Selected properties for the ATPAs are also set forth in Table 1, including acid number, amine number, softening point ("S.P.") and the appearance when combined at 20 wt % solids in PD-23™ petroleum distillate ("Appearance").

In preparing ATPAs, a 60/40 EDA/DTA equivalent ratio results in a material (ATPA A) that forms a clear, hard gel in PD 23 distillate (at 20% solids). Increasing this ratio to 75/25 (see ATPA B) and 80/20 (see ATPA C) decreases the ATPA's solubility in PD-23™ petroleum distillate, resulting in opaque, hard gels.

TABLE 1

PROPERTIES OF TERTIARY AMIDE-TERMINATED POLYAMIDES

| ATPA | Composition (eq. %) | Acid No. | Amine No. | S.P. (° C.) | Appearance |
|---|---|---|---|---|---|
| A. | 100% EMPOL ™ 1008; 60% EDA, 40% DTA | 20.8 | 25.1 | 82.2 | clear, hard gel |

TABLE 1-continued

PROPERTIES OF TERTIARY AMIDE-TERMINATED POLYAMIDES

| ATPA | Composition (eq. %) | Acid No. | Amine No. | S.P. (° C.) | Appearance |
|---|---|---|---|---|---|
| B. | 100% EMPOL ™ 1008; 75% EDA, 25% DTA | 11.3 | 10.9 | 101.9 | opaque, hard gel |
| C. | 100% EMPOL ™ 1008; 80% EDA, 20 DTA | 10.3 | 8.0 | 146.9 | opaque, hard gel |

EXAMPLE 2

Lipstick

| | |
|---|---|
| ATPA, A, B or C from Example 1 | 25.0% |
| Parleam oil | 56.0% |
| Polyglyceryl-2 polyhydroxystearate | 10.0% |
| Pigments (brown iron oxide and titanium oxide) | 9.0% |

Preparation: The selected ATPA resin is solubilized (or dissolved) using the polyglyceryl-2 polyhydroxystearate in the Parleam oil at 100° C., then the pigments are added. The mixture is mixed using a deflocculation turbine (manufactured by Raynarle) then cast in lipstick moulds. The percentage values provided above are in weight percent based on the total weight of the composition.

EXAMPLE 3

Dry Eye-Shadow

| | |
|---|---|
| ATPA A, B, or C from Example 1 | 25.0% |
| Parleam oil | 35.1% |
| Glyceryl oleate | 31.25% |
| Pigments | qs 100.0% |

An eye-shadow in stick form is produced as in example 2, using the components set forth above.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A structured solid composition comprising at least one colorant, a liquid oil phase, and a gellant wherein the gellant is a tertiary amide-terminated polyamide resin (ATPA) of the formula (1):

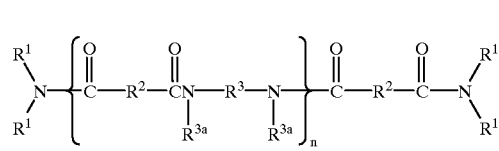

(1)

wherein, n designates a number of repeating units such that terminal amide groups constitute from 10% to 50% of the total amide groups;

$R^1$ at each occurrence is independently selected from a $C_{1-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid; the composition being essentially free of hydrocarbon wax; and the colorant, the liquid oil phase and the ATPA resin forming a physiologically acceptable medium:

2. The composition of claim 1 which is self-supporting.

3. The composition of claim 1 wherein $R^1$ at each occurrence is independently selected from a $C_{4-22}$ hydrocarbon group.

4. The composition of claim 1 wherein $R^2$ at each occurrence is independently selected from a $C_{4-42}$ hydrocarbon group.

5. The composition of claim 1 wherein $R^2$ at each occurrence is independently selected from a $C_{2-42}$ hydrocarbon group, where at least 50% of the $R_2$ groups have 30–42 carbon atoms.

6. The composition of claim 1 further comprising at least one liquid amphiphilic compound having, at ambient temperature, an HLB value of less than 12.

7. A structured composition comprising at least one colorant, a liquid oil phase and a gellant wherein the gellant is a tertiary amide-terminated polyamide (ATPA) resin of the formula (1):

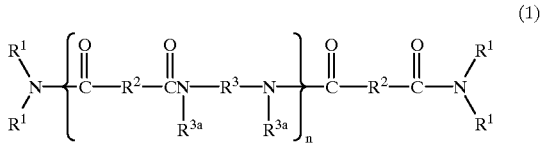

(1)

wherein, n designates a number of repeating units such that terminal amide groups constitute from 10% to 50% of the total amide groups;

$R^1$ at each occurrence is independently selected from a $C_{1-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid with a hardness of 20 to 2,000 g; the composition being essentially free of hydrocarbon wax; the colorant, the liquid oil phase and the ATPA resin forming a physiologically acceptable medium.

8. The composition of claim 7 having a hardness of from 20 g to 900 g.

9. The composition of claim 7 further comprising at least one liquid amphiphilic compound having, at ambient temperature, an HLB value of less than 12.

10. The composition of claim 9 wherein the HLB value is from 1 to 5.

11. The composition of claim 9 wherein the amphiphilic compound comprises a polar part and a lipophilic part, wherein the lipophilic part comprises a carbon chain containing at least 8 carbon atoms.

12. The composition of claim 11 wherein the lipophilic part comprises 18 to 28 carbon atoms.

13. The composition of claim 11 wherein the polar part is the reaction product of a compound selected from alcohols and polyols containing 1 to 12 hydroxyl groups, polyoxyalkylenes up to 20 propoxylation moieties and up to 20 oxyethylene moieties.

14. The composition of claim 11 wherein the amphiphilic compound is selected from esters of hydroxystearate, oleate or isostearate with one or more of glycerol, sorbitan, methylglucose, and octyldodecanol.

15. The composition of claim 9 wherein the amphiphilic compound represents 0.1 to 36% of the total weight of the composition.

16. The composition of claim 15 wherein the amphiphilic compound represents 2 to 15% of the total weight of the composition.

17. The composition of claims 1 or 7 wherein the ATPA resin represents 0.5 to 80% of the total weight of the composition.

18. The composition of claims 1 or 7 wherein the ATPA resin represents 5 to 40% of the total weight of the composition.

19. The composition of claims 1 or 7 wherein the liquid oil phase contains more than 40% of one or more non-polar oils.

20. The composition of claims 1 or 7 wherein the liquid oil phase contains at least one hydrocarbon oil of mineral or synthetic origin.

21. The composition of claims 1 or 7 wherein the oil phase contains at least one non-polar oil chosen from parleam oil, isoparaffins, squalane, squalene and their mixtures.

22. The composition of claims 1 or 7 wherein the liquid oil phase represents 20 to 75% of the total weight of the composition.

23. The composition of claims 1 or 7 that is formulated as a composition for care and/or treatment and/or makeup of keratinous matter.

24. The composition of claims 1 or 7 further comprising at least one cosmetic or dermatological active ingredient.

25. The composition of claims 1 or 7 further comprising at least one additive selected from water, silicone fluids, antioxidants, essential oils, preservatives, neutralisers, liposoluble polymers, additives, insect repellents, flavors and their mixtures.

26. The composition of claims 1 or 7 that is in the form of a transparent anhydrous rigid gel.

27. The composition of claims 1 or 7 wherein the colorant represents 5 to 25% of the total weight of the composition.

28. A structured solid composition for making up the skin or lips, comprising at least one pigment in sufficient quantity for making up the skin or lips, a liquid oil phase, and a gellant, wherein the gellant is a tertiary amide-terminated polyamide (ATPA) resin of the formula (1):

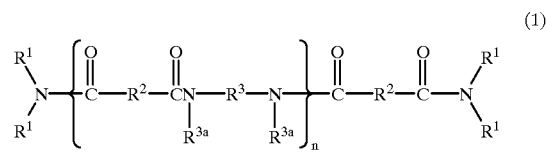

(1)

wherein, n designates a number of repeating units such that terminal amide groups constitute from 10% to 50% of the total amide groups;

$R^1$ at each occurrence is independently selected from a $C_{4-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid; wherein the pigment, the liquid oil phase and the ATPA resin form a physiologically acceptable medium.

29. The composition of claim 28 which is self-supporting.

30. A structured composition for making up the skin or lips, comprising at least one pigment in sufficient quantity for making up the skin or lips, a liquid oil phase, and a gellant, wherein the gellant is a tertiary amide-terminated polyamide (ATPA) resin of the formula (1):

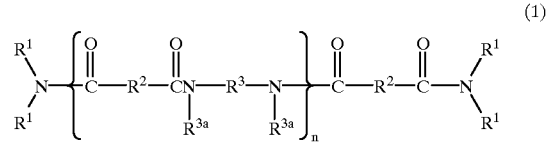

(1)

wherein, n designates a number of repeating units such that terminal amide groups constitute from 10% to 50% of the total amide groups;

$R^1$ at each occurrence is independently selected from a $C_{4-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a solid with hardness of 20 to 2000 g; and wherein the pigment, the liquid oil phase and the ATPA resin form a physiologically acceptable medium.

31. A structured lipstick composition comprising at least one pigment in sufficient quantity for making up the skin or lips, a liquid oil phase, and a gellant, wherein the gellant is a tertiary amide-terminated polyamide (ATPA) resin of the formula (1):

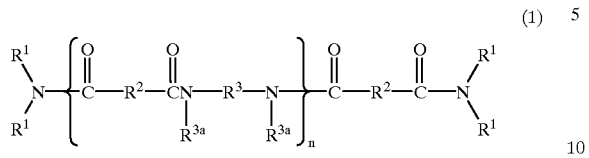

(1)

wherein,

- n designates a number of repeating units such that terminal amide groups constitute from 10% to 50% of the total amide groups;
- $R^1$ at each occurrence is independently selected from a $C_{4-22}$ hydrocarbon group;
- $R^2$ at each occurrence is independently selected from a $C_{2-42}$ hydrocarbon group;
- $R^3$ at each occurrence is independently selected from an organic group containing at least two carbon atoms in addition to hydrogen atoms, and optionally containing one or more oxygen and nitrogen atoms; and
- $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, the composition being in the form of a self-support solid; and the pigment, the liquid oil phase and the ATPA resin form a physiologically acceptable medium.

32. A stick for making up the skin or lips, comprising at least one pigment in sufficient quantity for making up the skin or lips, a liquid oil phase, and a gellant, wherein the gellant is a tertiary amide-terminated polyamide (ATPA) resin of the formula (1):

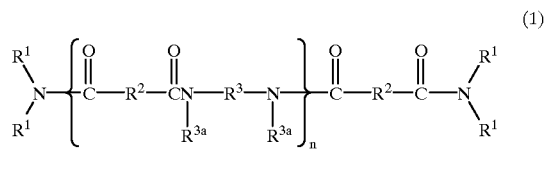

(1)

wherein,

- n designates a number of repeating units such that terminal amide groups constitute from 10% to 50% of the total amide groups;
- $R^1$ at each occurrence is independently selected from a $C_{4-22}$ hydrocarbon group;
- $R^2$ at each occurrence is independently selected from a $C_{2-42}$ hydrocarbon group;
- $R^3$ at each occurrence is independently selected from an organic group containing at least two carbon atoms in addition to hydrogen atoms, and optionally containing one or more oxygen and nitrogen atoms; and
- $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, and wherein the pigment, the oil phase and the ATPA resin form a physiologically acceptable medium.

* * * * *